United States Patent [19]

Adachi et al.

[11] Patent Number: 4,576,913

[45] Date of Patent: Mar. 18, 1986

[54] NAD(P)-INDEPENDENT GLYCEROL DEHYDROGENASE, A PROCESS FOR THE PREPARATION THEREOF AND THE USE THEREOF FOR THE DETERMINATION OF GLYCEROL AND TRIGLYCERIDES

[75] Inventors: Osao Adachi; Minoru Ameyama, both of Yamaguchi, Japan

[73] Assignee: Boehringer Mannheim GmbH, Mannheim, Fed. Rep. of Germany

[21] Appl. No.: 592,708

[22] Filed: Mar. 23, 1984

[30] Foreign Application Priority Data

Mar. 25, 1983 [DE] Fed. Rep. of Germany ....... 3311027

[51] Int. Cl.$^4$ .................. C12Q 1/00; C12Q 1/32; C12N 9/04; C12R 1/01; C12R 1/02
[52] U.S. Cl. .................................... 435/26; 435/4; 435/190; 435/822; 435/823
[58] Field of Search ............... 435/4, 26, 190, 822, 435/823

[56] References Cited

U.S. PATENT DOCUMENTS 2,948,658  8/1960  Green .......................... 435/823
4,223,090  9/1980  Mazza ......................... 435/26

FOREIGN PATENT DOCUMENTS 0647693  8/1962  Canada ........................ 435/823
0033603  3/1980  Japan ............................ 435/4
0008685  1/1981  Japan .......................... 435/190
113181   7/1983  Japan ........................... 435/26
1441642  7/1976  United Kingdom ............ 435/26

OTHER PUBLICATIONS

Chemical Abstracts: 91: 106580h Yamada, et al., *J. Ferment. Technol.* 1979, 57(3) 221-6.

Hemme, D. et al., Chemical Abstracts I: 94(19): 152446d (1981).

Sarkar, S. R., Chemical Abstracts II: 98(13) :105259t (1982).

Yamada, Shigeki et al., Chemical Abstracts III: 88(1): 2162v (1977).

Merck Index, ninth edition, pp. 2511, 6170 and 5192.

*Primary Examiner*—Sam Rosen
*Assistant Examiner*—Louanne C. Krawczewicz
*Attorney, Agent, or Firm*—Felfe & Lynch

[57] ABSTRACT

The present invention provides a new NAD(P)-independent glycerol dehydrogenase and a process for obtaining it, wherein a micro-organism of the species Pseudomonas, Serratia, Klebsiella, Erwinia, Aspergillus, Penicillium, Rhizopus, Acetobacter or Gluconobacter which is capable of forming this enzyme is cultured in a nutrient medium and the enzyme isolated from the culture broth.

The present invention also provides processes for the determination of glycerol and of triglycerides which make use of this new enzyme.

11 Claims, No Drawings

NAD(P)-INDEPENDENT GLYCEROL DEHYDROGENASE, A PROCESS FOR THE PREPARATION THEREOF AND THE USE THEREOF FOR THE DETERMINATION OF GLYCEROL AND TRIGLYCERIDES

The present invention is concerned with a new NAD(P)-independent glycerol dehydrogenase, with a process for the preparation thereof and with the use thereof for the determination of glycerol and triglycerides.

Glycerol dehydrogenases catalyze the reaction of glycerol with the formation of dihydroxyacetone. The previously known glycerol dehydrogenases are glycerol-NAD(P)-oxidoreductases (E.C.1.1.1.6, E.C.1.1.1.72 or E.C.1.1.1.156) which require NAD or NADP in oxidized form as co-enzyme. The reaction can be illustrated by the following equation:

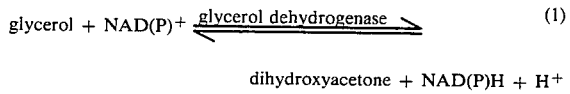

$$\text{glycerol} + \text{NAD(P)}^+ \xrightleftharpoons{\text{glycerol dehydrogenase}} \text{dihydroxyacetone} + \text{NAD(P)H} + \text{H}^+ \quad (1)$$

Equation (1) represents an equilibrium reaction, i.e. the NAD(P)-dependent glycerol dehydrogenase catalyses in the same way the formation of glycerol from dihydroxyacetone. If, therefore, equation (1) is used for the determination of glycerol or of the glycerol dehydrogenase activity, it is necessary to displace the equilibrium, by the addition of excess amounts of NAD(P), in the direction of dihydroxyacetone. The result of this is that this method of determination is relatively laborious and expensive. Small amounts of glycerol or of glycerol dehydrogenase activities cannot be measured exactly in this way. Furthermore, it is disadvantageous that the hydrogen cannot readily be transferred from the NAD(P)H to an appropriate redox indicator system. For this purpose, a further enzyme is necessary, for example diaphorase, in order to transfer the hydrogen from NADH to a tetrazolium salt with the formation of formazane.

It is an object of the present invention to provide a new glycerol dehydrogenase which does not suffer from the above-mentioned disadvantages and with the help of which glycerol can consequently be determined in a simple and inexpensive manner and small amounts of glycerol can also be detected in as quantitative a manner as possible.

Thus, according to the present invention, there is provided an NAD(P)-independent glycerol dehydrogenase which catalyses the following reaction:

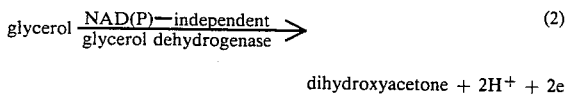

$$\text{glycerol} \xrightarrow{\text{NAD(P)-independent glycerol dehydrogenase}} \text{dihydroxyacetone} + 2\text{H}^+ + 2e \quad (2)$$

The two protons and electrons are thereby transferred to appropriate hydrogen and electron acceptors without the concurrent action of NAD or NADP as coenzyme. Since reaction (2) proceeds completely in the direction of the formation of dihydroxyacetone, the new enzyme permits glycerol and also triglycerides (after saponification thereof to glycerol and free fatty acids) to be determined simply and exactly.

In this manner, it is also possible to determine very small amounts of glycerol and thus also of triglycerides.

The microdetermination of glycerol and of triglycerides with the help of the enzyme according to the present invention can take place not only by the end point method but also by the kinetic method.

The NAD(P)-independent glycerol dehydrogenase according to the present invention can be characterised in more detail by the following properties:

1. Action

It dehydrogenates glycerol to give dihydroxyacetone, the two protons and two electrons thereby split off being transferred to appropriate acceptors without the concurrent action of NAD(P) as co-enzyme.

2. Substrate specificity

To a large extent, the new enzyme reacts specifically with glycerol. Especially with regard to structurally related substances normally also occurring in body fluids, no or only a slight activity is ascertainable. The following Table sets out the activities with regard to different substrates, the activity towards glycerol being taken as being 100:

TABLE
Relative activity of the glycerol dehydrogenase according to the present invention towards various substrates (glycerol = 100)

| substrate | relative activity |
|---|---|
| glycerol | 100 |
| D-sorbitol | 45 |
| D-mannitol | 26 |
| D-glucose | 0 |
| D-fructose | 0 |
| ethanol | 0 |

3. pH optimum and stable pH range

The optimum pH range of the enzyme according to the present invention is from 7.0 to 8.5. The highest activity is achieved at a pH of approximately 7.5. The enzyme is stable in the pH range of from 6.0 to 10.0.

4. Temperature optimum of the enzymatic action

The enzyme according to the present invention displays its highest activity in the temperature range of from 25° to 37° C.

5. Inhibition and activation

Oxamate has a slight inhibiting action on the enzyme. Phospholipids increase the activity of the glycerol dehydrogenase according to the present invention by about 20%.

The glycerol dehydrogenase according to the present invention can be produced from a whole series of micro-organisms, for example Pseudomonas, Serratia, Klebsiella, Erwinia, Aspergillus, Penicillium, Rhizopus, Acetobacter and Gluconobacter species. The enzyme according to the present invention is obtained in especially good yields from micro-organisms of the Acetobacter and Gluconobacter species, for example from *Acetobacter xylinus* DSM 2623 (IFO-3288), *Gluconobacter cerinus* DSM 2622 (IFO-3268) and *Gluconobacter industrius* DSM 2621 (IFO-3260). The mentioned micro-organism strains have been deposited in the German Collection of Micro-organisms under the give DSM numbers and in the Institute for Fermentation of Osaka under the IFO numbers given in brackets.

In order to produce the enzyme according to the present invention, an appropriate micro-organism is cultured according to known methods in a culture medium. As culture medium there can be used any conventional culture medium which is generally known as a source of nutrition for bacterial cultures.

As sources of carbon there can, in particular, be used various metabolizable carbon compounds, for example glucose, fructose, sucrose, maltose, saccharides with 5 carbon atoms, molasses and organic acids (for example gluconic acid and acetic acid), alcohols (for example glycerol and ethanol) and also sugar alcohols (for example mannitol and sorbitol).

As sources of nitrogen there can be used various kinds of nitrogen compounds, for example yeast extract, diluted casein, corn steep liquor, meat extract (natural materials), urea and ammonium salts.

As appropriate inorganic compounds, there can be added to the culture medium sodium salts, potassium salts, calcium salts and magnesium salts, as well as various phosphates.

The culturing of the micro-organisms for the production of the enzyme according to the present invention is preferably carried out in a liquid phase. However, on a technical scale, submerged cultures are especially preferred.

The bacterial culture for the production of the enzyme according to the present invention is preferably maintained in the temperature range of from 28° to 32° C. However, the temperature can also be changed so long as the micro-organisms grows and the desired enzyme can be produced.

The culturing period depends upon the culture conditions. Usually, a maximum enzyme yield is obtained when the culturing is terminated after about 1 to 3 days.

The pH value of the culture solution is not especially critical. It is preferably adjusted to the pH range of from 6 to 7.

Working up of the bacterial mass with the desired enzyme can take place according to conventional methods. The bacterial mass can be separated from the liquid medium for example by low pressure filtration or also by centrifuging. Known methods are also employed for breaking up the micro-organism cells. Thus, for example, the collected bacterial mass can be suspended in an appropriate buffer and then broken up with the help of ultrasonics, of a French press or of a Dyno-mill. The enzyme according to the present invention is present in the membrane fraction, which can be separated off by high speed centrifuging (90 minutes at 27,000 r.p.m.). By the addition of an appropriate detergent, also in an appropriate buffer system, the enzyme can be dissolved out of the membrane fraction.

The glycerol dehydrogenase according to the present invention is obtained from the solution obtained by processes conventionally employed for the isolation of enzymes. Thus, for example, in an advantageous manner, the enzyme according to the present invention can be isolated in pure form by column chromatography on ion exchangers, such as carboxymethyl- or DEAE-cellulose, by column chromatography on hydroxylapatite or also by gel filtration on "Sephadex".

The activity of the enzyme according to the present invention is expressed in international units (U/mg.) at 25° C., pH 7.5, with glycerol, phenazine methosulphate and 2,6-dichlorophenol-indophenol as substrate.

The NAD(P)-independent glycerol dehydrogenase according to the present invention can be used in an advantageous manner for the determination of glycerol according to equation (2). According to this reaction equation, two atoms of hydrogen are removed from one molecule of glycerol in order to form one mole of dihydroxyacetone. The two protons and the two electrons are transferred to appropriate hydrogen acceptors (A). There is thus given the following extended reaction equation:

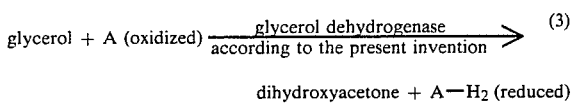

$$\text{glycerol} + \text{A (oxidized)} \xrightarrow[\text{according to the present invention}]{\text{glycerol dehydrogenase}} \text{dihydroxyacetone} + \text{A}-\text{H}_2 \text{ (reduced)} \quad (3)$$

According to equation (3), not only glycerol but also the glycerol dehydrogenase activity can be determined by measuring either the decrease of the oxidised acceptor (A) or the increase of the reduced acceptor (A) or the amount of dihydroxyacetone formed.

Consequently, the present invention also provides a process for the determination of glycerol, wherein glycerol is converted into dihydroxyacetone in the presence of an NAD(P)-independent glycerol dehydrogenase, two protons and two electrons thereby being transferred directly to appropriate acceptors and the decrease of an acceptor in the oxidised form or the increase of an acceptor in the reduced form or the increase of dihydroxyacetone being measured.

As acceptors (A), there can be used all substances which are able to take up electrons and protons. If the acceptor is to be used as indicator for the enzymatic reaction, then it must display a measurable change in the conversion of the oxidized form into the reduced form. Such acceptors are preferred which display a visible change in the conversion of the oxidized form into the reduced form which, in the ideal case, is from colourless to coloured or vice versa. If, in the case of the redox conversion, the acceptor does not display a measurable change, the first acceptor redox system can be coupled with a second redox system which, in turn, displays a measurable redox process.

As acceptor in the sense of being usable according to the present invention, there can be used, for example, oxygen which is thereby converted into water or into another reduced form of oxygen. The oxygen consumption can be measured in conventional manner, for example with the help of an oxygen electrode or of a Warburg manometer. The consumed amount of oxygen is proportional to the amount of glycerol present in the sample.

The amount of glycerol present in the sample can also be determined in known manner by measurement of the dihydroxyacetone formed. In this case, too, a number of known processes are available (cf. in this regard, for example, E. B. Sanders and J. Schubert, Anal. Chem., 43, p.59 et seq/1971).

The use of acceptors which, upon conversion from the oxidized form into the reduced form, undergo a colour change is especially advantageous. Such colour changes can be measured in a simple and dependable way with the help of spectrometric methods.

In the following, there are given some examples of acceptor systems which can be used according to the present invention, the redox process of which can be measured directly or can be made measurable by coupling with a further redox system:

1. The $Fe^{2+}/Fe^{3+}$ system

For this purpose, there can be used potassium ferricyanide which, by taking up an electron, is converted into the colourless potassium ferrocyanide. The deep blue-coloured complex Berlin Blue is formed with ferric ions, i.e.:

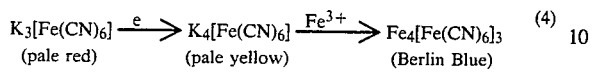

$$K_3[Fe(CN)_6] \xrightarrow{e} K_4[Fe(CN)_6] \xrightarrow{Fe^{3+}} Fe_4[Fe(CN)_6]_3 \quad (4)$$
(pale red)    (pale yellow)    (Berlin Blue)

Ferric salts can also be added directly. The ferrous ions arising from the reduction can be detected by complex formation with appropriate dyestuffs, for example bis-dimethylglyoxime or also 1,10-phenanthroline:

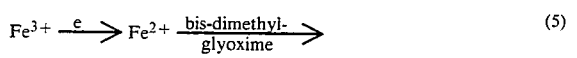

$$Fe^{3+} \xrightarrow{e} Fe^{2+} \xrightarrow{bis\text{-}dimethyl\text{-}glyoxime} \quad (5)$$

$$Fe^{2+}-bis\text{-}dimethylglyoxime \text{ (red)}$$

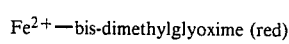

$$Fe^{3+} \xrightarrow{e} Fe^{2+} \xrightarrow{1,10\text{-}phenanthroline} \quad (6)$$

$$Fe^{2+}-1,10\text{-}phenanthroline \text{ (ferroin, red)}$$

2. Di- or triarylmethane dyestuffs

The general reaction scheme for this redox system can be illustrated as follows:

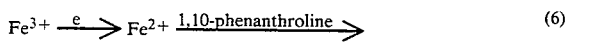

$$\text{oxidised form} \underset{\text{oxidation}}{\overset{\text{reduction}}{\rightleftarrows}} \text{reduced form}$$
(coloured)    (leuco base, colourless)

As representatives of this class of dyestuffs, there may be mentioned malachite green, crystal violet, Coomassie blue and the leuco bases thereof.

3. Phenazine-methosulphate (PMS)

General equation:

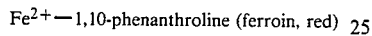

$$PMS \text{ (ox.)} \xrightarrow{+2H^{\oplus} + 2e} PMS \text{ (red.)} \quad (7)$$

The conversion of the oxidised form of PMS into its reduced form can only be measured with difficulty. It is advantageous to couple this redox system with another redox system. Coupling with tetrazolium salts has proved to be useful. The general reaction scheme can then be given as follows:

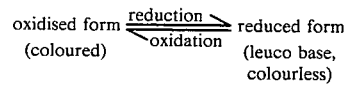

$$PMS \text{ (red.)} + \text{tetrazolium salt} \longrightarrow PMS \text{ (ox.)} + \text{formazane} \quad (8)$$
(oxidised form, colourless)    (reduced form, coloured)

As tetrazolium salts, there can, for example, be used the following:
INT: 2-(p-iodophenyl)-3-(p-nitrophenyl)-5-phenyltetrazolium chloride
MTT: 3-(4',5'-dimethylthiazol-2-yl)-2,4-diphenyltetrazolium bromide
NBT: 2,2'-di-(p-nitrophenyl)-5,5'-diphenyl-3,3'-(3,3'-dimethoxy-4,4'-diphenylene)-ditetrazolium chloride.
PMS can also be coupled in an advantageous manner with 2,6-dichlorophenol-indophenol (DCIP). There is then given the following redox scheme:

$$PMS \text{ (red.)} + DCIP \text{ (ox.)} \longrightarrow PMS \text{ (ox.)} + DCIP \text{ (red.)} \quad (9)$$

4. Indigo and indigo derivatives

Indigo and its derivatives also act as hydrogen acceptors. The following general scheme applies:

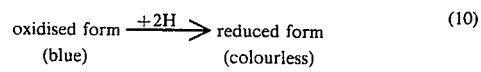

$$\text{oxidised form} \xrightarrow{+2H} \text{reduced form} \quad (10)$$
(blue)    (colourless)

Indigo derivatives which can be used according to the present invention include, for example, 6,6'-dibromoindigo and 5,5',7,7'-tetrabromoindigo.

5. Phenoxazine and phenothiazine dyestuffs

Phenoxazine and phenothiazine dyestuffs are also able to take up hydrogen atoms and thereby change from a coloured oxidised form into a colourless reduced form:

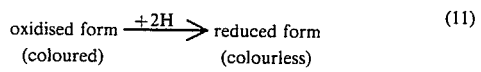

$$\text{oxidised form} \xrightarrow{+2H} \text{reduced form} \quad (11)$$
(coloured)    (colourless)

As an example of this class of dyestuff, there may be mentioned methylene blue which, by taking up two hydrogen atoms per molecule, is converted into leucomethylene blue.

The above-described methods for the determination of glycerol can also be advantageously used for the determination of substances which can be converted into glycerol, as well as for the determination of enzymes which catalyse such reactions.

As an example of the mentioned possibilities of use, there is explained in more detail the determination of triglycerides in blood, plasma and serum. For this purpose, the triglycerides (neutral fats) are hydrolysed in known manner with the help of an appropriate lipase and the liberated glycerol is reacted with the help of the glycerol dehydrogenase according to the present invention and appropriate electron and hydrogen acceptors in the above-described manner. The reaction sequence can be illustrated as follows:

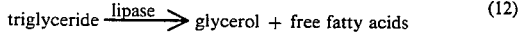

$$\text{triglyceride} \xrightarrow{\text{lipase}} \text{glycerol} + \text{free fatty acids} \quad (12)$$

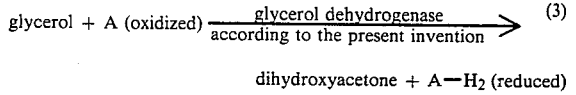

$$\text{glycerol} + A \text{ (oxidized)} \xrightarrow[\text{according to the present invention}]{\text{glycerol dehydrogenase}} \quad (3)$$

$$\text{dihydroxyacetone} + A-H_2 \text{ (reduced)}$$

The enzymatic hydrolysis of the triglycerides is carried out according to known methods. As enzymes for the saponification of the triglycerides, there can advantageously be used the commercially available lipoprotein lipase (E.C. 3.1.1.34) or a mixture of lipase (E.C. 3.1.1.3) and esterase (E.C. 3.1.1.1).

Glucose in the blood does not influence the determination of glycerol and of triglycerides with the help of the NAD(P)-independent glycerol dehydrogenase according to the present invention.

The following Examples are given for the purpose of illustrating the present invention:

EXAMPLE 1

NAD(P)-independent glycerol dehydrogenase from *Gluconobacter industrius* DSM 2621 (IFO-3260)

*Gluconobacter industrius* DSM 2621 is cultured in a glycerol-glutamic acid medium according to known methods. The bacterial mass is collected and broken up in a French press at a pressure of 1000 kg./cm$^2$. The unbroken cells are removed by centrifuging (5000 g). The cell homogenate is centrifuged for 90 minutes in an ultracentrifuge (68,000 g). The cell membrane fraction is collected. It is adjusted with 0.05M tris-HCl buffer (pH 8.0) to a content of 10 mg. protein/ml. A conventional, appropriate detergent is added, for example Triton X 100, in order to achieve an end concentration of 0.5%. The mixture obtained is stirred for 60 minutes at 0° C. in order to bring the enzyme into solution. Subsequently, it is centrifuged for 60 minutes (68,000 g). From the supernatant, after chromatography on DEAE-cellulose (pH 7.5) and hydroxylapatite (pH 7.5), there is obtained a uniform enzyme preparation with an activity of 50 U/mg.

EXAMPLE 2

Instead of the *Gluconobacter industrius* DSM 2621 micro-organism used in Example 1, there is cultured and worked up *Acetobacter xylinus* DSM 2623 or *Gluconobacter cerinus* DSM 2622 in the manner described in Example 1. Enzyme preparations are obtained with an activity of 42 U/mg. and 46 U/mg., respectively.

EXAMPLE 3

Determination of the enzyme activity of the glycerol dehydrogenase according to the present invention 0.6 μmole phenazine methosulphate, 0.6 μmole 2,6-dichlorophenol-indophenol and 100 μmole tris-HCl buffer (pH 7.5) are placed in a cuvette. The enzyme preparation to be determined, the activity of which is within the range of from 0.01 to 0.1 units, is added thereto. An end volume of 2.9 ml. is obtained by the addition of double distilled water. After incubation at 25° C. for 5 minutes, the enzyme reaction is started by the addition of 100 μmole glycerol. The speed of decolorization of 2,6-dichlorophenol-indophenol is followed by measurement of the absorption at 600 nm. The calculation of the enzyme activity takes place in that, as millimolar absorption coefficient for 2,6-dichlorophenol-indophenol at pH 7.5, there is assumed a value of 100. The amount of enzyme which brings about an absorption change of $\Delta E_{600}=2.33$/min. is taken as being one unit.

EXAMPLE 4

Determination of glycerol with phenazine methosulphate and 2,6-dichlorophenol-indophenol 1. Production of a calibration curve Seven different standard solutions containing 0.01, 0.02, 0.04, 0.06, 0.08, 0.10 and 0.50 μmoles glycerol, in 0.1 ml solution are prepared from a standard 100 μmole/liter glycerol solution using doubly distilled water. To each of these glycerol standard solutions is added 0.1 ml. of an enzyme solution with an activity of 10 U. In each case, an end volume of 2.8 ml. is obtained by the addition of double distilled water. The solutions are then incubated for 5 minutes at 25° C.

Thereafter, the reaction is started by the addition of 0.2 ml. of a solution which contains 0.6 μmole phenazine methosulphate and 0.6 μmole 2,6-dichlorophenol-indophenol. The absorption is measured at 600 nm with a spectrophotometer. In the range of from 0.01 to 0.05 μmole glycerol, there is observed a linear course.

2. Measurement of an unknown sample 2 ml. of a sample with an unknown glycerol content are mixed in a cuvette with 2 ml. of solution which contains 0.6 μmole phenazine methosulphate and 0.6 μmole 2,6-dichlorophenol-indophenol. It is mixed with 0.5 ml. tris-HCl buffer (pH 7.5) (100 μmole) and incubated for 5 minutes at 25° C. The detection reaction is started by the addition of 0.1 ml. of an enzyme solution with an activity of 10 U. The decrease of the absorption at 600 nm is measured. By comparison of the measured absorption difference with the calibration curve, there is determined the glycerol content of the sample used.

EXAMPLE 5

Determination of glycerol with phenazine methosulphate and a tetrazolium salt 1 ml. of a sample with an unknown glycerol content is mixed in a cuvette with 2 ml. of a solution which contains 0.1 μmole phenazine methosulphate, 1.2 μmole 3-(4,5-dimethylthiazol-2-yl)-2,5-diphenyltetrazolium bromide and 100 μmole tris-HCl buffer (0.1M; pH 7.5). It is incubated for 5 minutes at 25° C. The detection reaction is started by the addition of 20 μl. of a solution with 1 U of the enzyme according to the present invention. The absorption change at 570 nm is measured. The glycerol content of the sample is determined by comparison of the measured absorption difference with a calibration curve, which can be produced by the measurement of samples with known glycerol contents.

EXAMPLE 6

Determination of triglycerides 0.02 ml. of human serum is mixed in a cuvette with 0.5 ml. of an enzyme solution which contains 100 to 200 U lipoprotein lipase or a mixture of lipase and esterase and incubated for 20 minutes at 25° C. Thereafter, 2 ml. of a solution are added which contains 0.6 μmole phenazine methosulphate, 0.2 μmole 2,6-dichlorophenol-indophenol and 100 μmole tris-HCl buffer (pH 7.5). Thereafter, incubation is carried out for 5 minutes at 25° C. The detection reaction is then started by the addition of 0.1 ml. of a solution which contains 1 U of the glycerol dehydrogenase according to the present invention. The absorption decrease is measured at 600 nm. From the absorption difference, there can be determined, in the manner described in Example 4, the glycerol content and thus the triglyceride content. An average triglyceride content of 110 mg./dl. is found.

In carrying out the determination of triglycerides, it is recommended to carry out a blank determination.

It will be understood that the specification and examples are illustrative but not limitative of the present invention and that other embodiments within the spirit and scope of the invention will suggest themselves to those skilled in the art.

What is claimed is:

1. Glycerol dehydrogenase which catalyzes the reaction of glycerol to dihydroxyacetone characterized in that said glycerol dehydrogenase is NAD(P)-independent.

2. Process for obtaining an NAD(P)-independent glycerol dehydrogenase comprising culturing, in a nutrient medium, a micro-organism of the species Pseudomonas, Serratia, Klebsiella, Erwinia, Aspergillus, Penicillium, Rhizopus, Acetobacter or Gluconobacter which is capable of forming this enzyme and isolating enzyme from the culture broth.

3. Process according to claim 2, wherein the micro-organism used is *Acetobacter xylinus* DSM 2623, *Gluconobacter cerinus* DSM 2622 or *Gluconobacter industrius* DSM 2621.

4. NAD(P)-independent glycerol dehydrogenase, obtained by the process of claim 2.

5. Process for the determination of glycerol, comprising converting glycerol into dihydroxyacetone with an NAD(P)-independent glycerol dehydrogenase according to claim 1 in the presence of a proton and electron acceptor, and measuring the decrease of the oxidised acceptor or the increase of the reduced acceptor or the increase of dihydroxyacetone as a measure of the glycerol.

6. Process according to claim 5, wherein oxygen is used as the acceptor and the consumption of oxygen is measured.

7. Process according to claim 5, wherein a first acceptor redox system is coupled with a further redox indicator.

8. Process according to claim 7, wherein the first acceptor is phenazine methosulphate and the further redox indicator is 2,6-dichlorophenol-indophenol, the absorption decrease of 2,6-dichlorophenol-indophenol being measured at 600 nm.

9. Process according to claim 7, wherein the first acceptor is phenazine methosulphate and the further redox indicator is a tetrazolium salt, the formazane formation being measured photometrically.

10. Process for the determination of triglycerides, comprising saponifying the triglycerides to glycerol and free fatty acids converting the free glycerol into dihydroxyacetone with an NAD(P)-independent glycerol dehydrogenase according to claim 1 in the presence of a proton and electron acceptor, and measuring the decrease of the oxidised acceptor or the increase of the reduced acceptor or the increase of dihydroxyacetone as a measure of the glycerol.

11. Agent for the determination of glycerol, by means of which glycerol is reacted with the help of a glycerol dehydrogenase in the presence of an appropriate acceptor to give dihydroxyacetone, the decrease of the oxidised acceptor or the increase of the reduced acceptor or the increase of dihydroxyacetone being measurable, said agent comprising an NADP-independent glycerol dehydrogenase according to claim 1 and a means for the determination of the decrease of the oxidised acceptor or the increase of the reduced acceptor or the increase of the dihydroxyacetone.

* * * * *

UNITED STATES PATENT AND TRADEMARK OFFICE
CERTIFICATE OF CORRECTION

PATENT NO. : 4,576,913

DATED : March 18, 1986

INVENTOR(S) : Osao Adachi et al

It is certified that error appears in the above-identified patent and that said Letters Patent is hereby corrected as shown below:

Claim 4, line 2: Please change "2" to -- 3 --.

Signed and Sealed this

Twenty-fifth Day of November, 1986

*Attest:*

DONALD J. QUIGG

*Attesting Officer*     *Commissioner of Patents and Trademarks*